United States Patent
Heroux et al.

(10) Patent No.: US 10,188,826 B2
(45) Date of Patent: Jan. 29, 2019

(54) CATHETERS INCLUDING ANTIMICROBIAL SLEEVE AND METHODS OF MAKING CATHETERS

(75) Inventors: Lise-Helene Heroux, Plainville, MA (US); Adin M. Potter, South Glens Falls, NY (US); Robert Frechette, Lakeville, MA (US); Manisha M. Dadhania, Boston, MA (US)

(73) Assignee: Covidien LP, Mansfield, MA (US)

( * ) Notice: Subject to any disclaimer, the term of this patent is extended or adjusted under 35 U.S.C. 154(b) by 1574 days.

(21) Appl. No.: 11/529,672

(22) Filed: Sep. 29, 2006

(65) Prior Publication Data

US 2008/0172011 A1     Jul. 17, 2008

(51) Int. Cl.
| | |
|---|---|
| *A61M 25/00* | (2006.01) |
| *A61L 29/06* | (2006.01) |
| *A61L 29/16* | (2006.01) |
| *A61M 39/02* | (2006.01) |
| *A61M 25/06* | (2006.01) |

(52) U.S. Cl.
CPC ............. *A61M 25/00* (2013.01); *A61L 29/06* (2013.01); *A61L 29/16* (2013.01); *A61M 25/0017* (2013.01); *A61M 25/0029* (2013.01); *A61M 25/0045* (2013.01); *A61L 2300/104* (2013.01); *A61L 2300/404* (2013.01); *A61L 2300/42* (2013.01); *A61L 2300/61* (2013.01); *A61M 2025/0056* (2013.01); *A61M 2025/0057* (2013.01); *A61M 2025/0098* (2013.01); *A61M 2025/0681* (2013.01); *A61M 2039/0285* (2013.01)

(58) Field of Classification Search
CPC .. A61M 2025/0056; A61M 2025/0681; A61M 2025/0098; A61M 25/0017; A61M 25/0045; A61M 25/0029; A61M 2039/0285
USPC .................. 604/264–265, 500, 158; 424/423
See application file for complete search history.

(56) References Cited

U.S. PATENT DOCUMENTS

| | | | |
|---|---|---|---|
| 3,566,874 | A | 3/1971 | Shepherd et al. |
| 3,598,127 | A | 8/1971 | Wepsic |
| 3,699,956 | A | 10/1972 | Kitrilakis et al. |
| 4,054,139 | A | 10/1977 | Crossley |

(Continued)

FOREIGN PATENT DOCUMENTS

| | | |
|---|---|---|
| CN | 2572987 Y | 9/2003 |
| DE | 3916648 C1 | 9/1990 |

(Continued)

OTHER PUBLICATIONS

JP Office Action for corresponding Japanese Application No. 2007-252753 dated Jun. 15, 2012, and English translation thereof.

(Continued)

*Primary Examiner* — Nathan R Price
*Assistant Examiner* — Anh Bui
(74) *Attorney, Agent, or Firm* — Kenneth Collier; Jessica Kwak Rauckman (57) ABSTRACT

A catheter includes a tubular body having an outer surface, and a sleeve disposed on only a portion of the outer surface of the tubular body. The sleeve includes an outer layer overlying an inner layer. The catheter contains a water-soluble, anti-microbial agent in the outer layer of the sleeve. Methods of making the catheter are also disclosed.

48 Claims, 4 Drawing Sheets

(56) References Cited

U.S. PATENT DOCUMENTS

| | | | |
|---|---|---|---|
| 4,515,593 A | 5/1985 | Norton | |
| 4,592,920 A | 6/1986 | Murtfeldt | |
| 4,603,152 A | 7/1986 | Laurin et al. | |
| 4,612,337 A | 9/1986 | Fox, Jr. et al. | |
| 4,623,329 A | 11/1986 | Drobish et al. | |
| 4,676,782 A | 6/1987 | Yamamoto et al. | |
| 4,677,143 A * | 6/1987 | Laurin | A01N 25/10 106/15.05 |
| 4,678,660 A | 7/1987 | McGary et al. | |
| 4,713,402 A | 12/1987 | Solomon | |
| 4,906,466 A * | 3/1990 | Edwards et al. | 424/421 |
| 4,939,007 A | 7/1990 | Hu et al. | |
| 4,950,256 A | 8/1990 | Luther et al. | |
| 4,994,047 A * | 2/1991 | Walker | A61L 29/06 600/581 |
| 4,999,210 A | 3/1991 | Solomon et al. | |
| 5,013,306 A | 5/1991 | Solomon et al. | |
| 5,019,096 A | 5/1991 | Fox, Jr. et al. | |
| 5,049,140 A | 9/1991 | Brenner et al. | |
| 5,061,254 A | 10/1991 | Karakelle et al. | |
| 5,077,372 A | 12/1991 | Hu et al. | |
| 5,091,442 A | 2/1992 | Milner | |
| 5,102,401 A * | 4/1992 | Lambert et al. | 604/264 |
| 5,135,516 A * | 8/1992 | Sahatjian et al. | 604/265 |
| 5,156,592 A * | 10/1992 | Martin | A61M 5/1582 604/175 |
| 5,165,952 A | 11/1992 | Solomon et al. | |
| 5,201,724 A | 4/1993 | Hukins et al. | |
| 5,236,422 A | 8/1993 | Eplett, Jr. | |
| 5,250,649 A | 10/1993 | Onwumere et al. | |
| 5,272,012 A | 12/1993 | Opolski | |
| 5,322,659 A | 6/1994 | Walder et al. | |
| 5,328,698 A | 7/1994 | Onwumere et al. | |
| 5,338,770 A | 8/1994 | Winters et al. | |
| 5,451,424 A | 9/1995 | Solomon et al. | |
| 5,470,585 A * | 11/1995 | Gilchrist | A01N 25/08 424/409 |
| 5,505,695 A | 4/1996 | Eplett, Jr. | |
| 5,538,510 A | 7/1996 | Fontirroche et al. | |
| 5,545,151 A * | 8/1996 | O'Connor et al. | 604/524 |
| 5,630,804 A | 5/1997 | Imada et al. | |
| 5,688,516 A | 11/1997 | Raad et al. | |
| 5,725,817 A * | 3/1998 | Milder | 264/104 |
| 5,762,638 A | 6/1998 | Shikani et al. | |
| 5,820,607 A | 10/1998 | Tcholakian et al. | |
| 5,848,995 A * | 12/1998 | Walder | 604/265 |
| 5,865,814 A | 2/1999 | Tuch | |
| 5,873,904 A * | 2/1999 | Ragheb | A61F 2/82 604/265 |
| 5,877,263 A | 3/1999 | Patnaik et al. | |
| 6,096,798 A | 8/2000 | Luthra et al. | |
| 6,107,416 A | 8/2000 | Patnaik et al. | |
| 6,143,318 A | 11/2000 | Gilchrist et al. | |
| 6,261,271 B1 | 7/2001 | Solomon et al. | |
| 6,273,875 B1 * | 8/2001 | Siman et al. | 604/264 |
| 6,406,687 B1 | 6/2002 | Luthra et al. | |
| 6,447,805 B1 | 9/2002 | Healy | |
| 6,887,270 B2 | 5/2005 | Miller et al. | |
| 7,034,061 B1 | 4/2006 | Luthra et al. | |
| 2002/0156430 A1 | 10/2002 | Haarala et al. | |
| 2002/0165492 A1 | 11/2002 | Davey et al. | |
| 2002/0169370 A1 * | 11/2002 | Kensey et al. | 600/370 |
| 2003/0065292 A1 | 4/2003 | Darouiche et al. | |
| 2003/0165647 A1 * | 9/2003 | Kaneko et al. | 428/36.3 |
| 2004/0068241 A1 | 4/2004 | Fischer, Jr. | |
| 2004/0086568 A1 | 5/2004 | Ditizio et al. | |
| 2004/0116551 A1 | 6/2004 | Terry | |
| 2004/0142016 A1 * | 7/2004 | Luthra et al. | 424/423 |
| 2004/0170752 A1 * | 9/2004 | Luthra | A61L 31/10 427/2.24 |
| 2004/0210208 A1 | 10/2004 | Paul et al. | |
| 2004/0220534 A1 * | 11/2004 | Martens et al. | 604/265 |
| 2004/0225264 A1 | 11/2004 | Bourne et al. | |
| 2004/0249338 A1 * | 12/2004 | DeCant et al. | 604/43 |
| 2005/0033222 A1 | 2/2005 | Haggstrom et al. | |
| 2005/0148928 A1 | 7/2005 | Molina et al. | |
| 2005/0214342 A1 * | 9/2005 | Tweden et al. | 424/423 |
| 2005/0245671 A1 * | 11/2005 | Moon | C08K 5/0058 524/543 |
| 2005/0261636 A1 * | 11/2005 | Rome et al. | 604/247 |
| 2005/0271698 A1 | 12/2005 | Bucay-Couto et al. | |
| 2006/0009806 A1 | 1/2006 | Heruth et al. | |
| 2006/0025726 A1 | 2/2006 | Fischer, Jr. et al. | |
| 2006/0039946 A1 | 2/2006 | Heruth et al. | |
| 2006/0045899 A1 | 3/2006 | Sarangapani | |
| 2006/0118121 A1 * | 6/2006 | Martens et al. | 128/207.14 |
| 2007/0129690 A1 * | 6/2007 | Rosenblatt | A61L 29/16 604/265 |

FOREIGN PATENT DOCUMENTS

| | | |
|---|---|---|
| EP | 1 161 268 B1 | 8/2005 |
| EP | 2119468 A1 | 11/2009 |
| JP | 03-029664 | 2/1991 |
| JP | 10-211272 | 8/1998 |
| JP | 10-323386 | 12/1998 |
| WO | WO 90/08470 | 8/1990 |
| WO | 98/54104 | 12/1998 |
| WO | 99/62834 | 12/1999 |
| WO | 99/62835 | 12/1999 |
| WO | WO 01/43788 A1 | 6/2001 |
| WO | WO 2004/096330 | 4/2004 |
| WO | 2007/111874 A2 | 10/2007 |

OTHER PUBLICATIONS

Office Action issued in Canadian Application No. 2,602,774 dated Oct. 2, 2013.

Office Action fro Chinese Appl. No. 201310073825.1 dated May 30, 2014.

First Office Action issued in Chinese Appl. No. 201210059962.5 dated Apr. 26, 2013.

* cited by examiner

CATHETERS INCLUDING ANTIMICROBIAL SLEEVE AND METHODS OF MAKING CATHETERS

BACKGROUND

Some known catheters are tubular, flexible devices adapted for administration of fluids (withdrawal, introduction, etc.) within a body. These catheters may be employed for the administration of fluids to a patient, such as by the introduction and withdrawal of fluid for applications, such as, surgery, treatment or diagnosis.

SUMMARY

An exemplary embodiment of a catheter comprises a tubular body having an outer surface; and a sleeve disposed on only a portion of the outer surface of the tubular body, the sleeve comprising an outer layer co-extruded on an inner layer, the catheter comprising a water-soluble, anti-microbial agent contained only in the outer layer of the sleeve.

An exemplary embodiment of a method of making a catheter comprises applying a sleeve over only a portion of an outer surface of a tubular body, the sleeve comprising an outer layer co-extruded on an inner layer, the catheter comprising a water-soluble, anti-microbial agent contained only in the outer layer of the sleeve.

DETAILED DESCRIPTION

Catheters and methods of making the catheters are provided. The catheters comprise an anti-microbial outer sleeve containing a water-soluble, anti-microbial agent. The catheters can have various constructions for different medical applications. For example, the catheters can be midline catheters; central venous catheters, such as hemodialysis catheters (chronic or acute); intravenous (IV) catheters; peripheral insert central catheters (PICC); urological catheters, such as Foley catheters, and the like. Some embodiments of the catheters can include a single lumen. Other embodiments of the catheters can include multiple lumens, such as two or three lumens.

Figure 1:
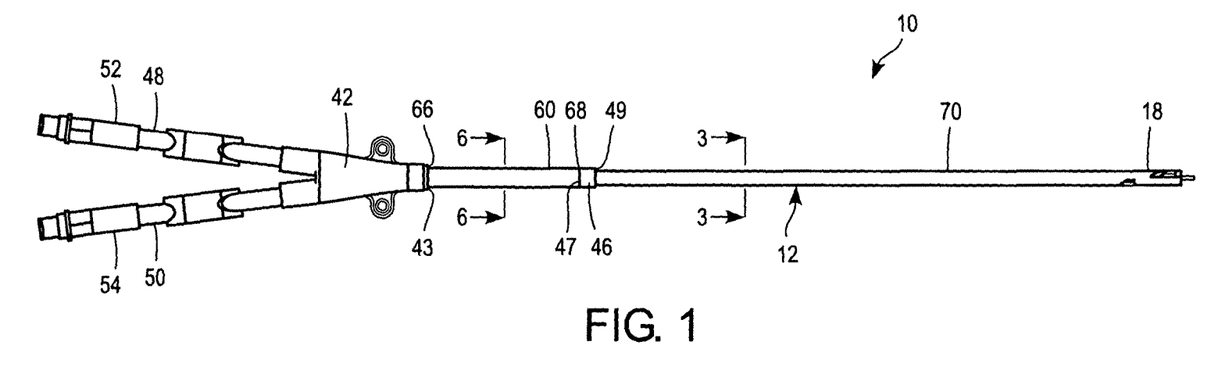
FIG. 1 is a top plan view of an exemplary embodiment of a catheter comprising an anti-microbial sleeve.
Figure 2:
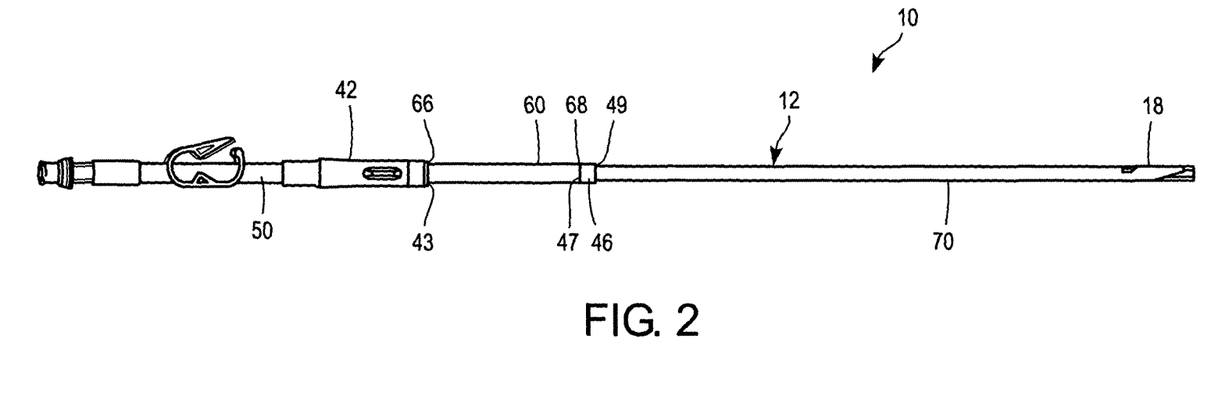
FIG. 2 is a side elevation view of the catheter illustrated in FIG. 1
Figure 3:
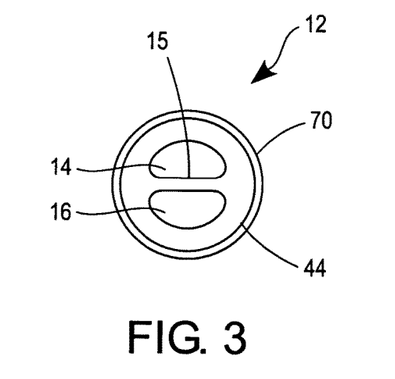
FIG. 3 is a cross-sectional view of the tubular body of the catheter in the direction of line 3-3 of FIG. 1, showing an anti-thrombogenic coating formed on the tubular body.

FIGS. 1 and 2 illustrate an exemplary embodiment of a catheter 10. The catheter 10 comprises an elongated tubular body 12. The tubular body 12 can be made of any suitable material that provides desired properties, such as polyurethane, and can have any suitable dimensions, depending on the type of the catheter 10. The tubular body 12 may include multiple liquid conduits (lumens) depending on the function of catheter (e.g., a dual-lumen or triple-lumen hemodialysis catheter). As shown in FIG. 3, the tubular body 12 includes two lumens 14, 16 separated by a septum 15 to allow fluid outflow in one axial direction through one lumen and fluid return flow in the opposite axial direction through the other lumen. The lumens 14, 16 can have any suitable cross-sectional shape and size that provides the desired bi-directional liquid flow characteristics through the lumens.

The catheter 10 can be used, for example, for the treatment of blood during a hemodialysis process in which toxins are removed from the body. The catheter 10 can be employed for simultaneous withdrawal and introduction of fluid with a body. One lumen can perform withdrawal of blood and the other lumen can introduce treated blood to the body. During an exemplary hemodialysis procedure, the catheter 10 is inserted into a body and blood is withdrawn through an arterial lumen of the catheter 10. This blood is supplied to a hemodialysis unit, which dialyzes, or cleans, the blood to remove waste and excess water. The dialyzed blood is returned to the patient through a venous lumen of the catheter 10.

Figure 4:
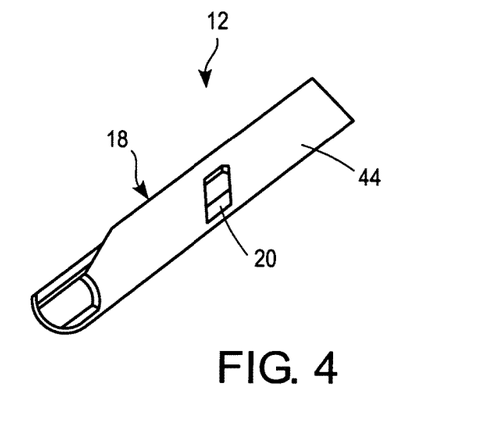
FIG. 4 illustrates a portion of the tubular body including the distal tip of the catheter illustrated in FIG. 1.

The tubular body 12 has a distal tip 18 at its distal end. In the exemplary embodiment, each lumen communicates with a single slot. FIG. 4 shows an elongated slot 20 associated with one of the two lumens 14, 16 formed in the outer wall of the tubular body 12. In the illustrated embodiment, the slots are formed in opposing sides of the tubular body 12.

In another exemplary embodiment, the catheter can comprise a tubular body having a three-lumen structure with a distal tip as disclosed in U.S. Patent Application Publication No. 2005/0033222, the entire disclosure of which is incorporated herein by reference.

As shown in FIGS. 1 and 2, the catheter 10 comprises a hub 42, which is provided on the outer surface 44 (FIG. 3) of the tubular body 12 at the proximal end of the tubular body 12. The hub 42 can be attached to the tubular body 12 in any suitable manner, such as by injection molding the hub 42 onto the tubular body 12 at the proximal end.

The illustrated catheter 10 comprises a tissue in-growth cuff 46 on the outer surface 44 of the tubular body 12 at a location spaced from the hub 42 in a direction toward the distal tip 18. The cuff 46 can be made of any suitable material, as is well known in the art, such as felt. Typically, the cuff 46 is provided on a chronic hemodialysis catheter.

Extension tubes 48, 50 are secured to the hub 42 at the back end of the catheter 10. Adapters 52, 54, such as luer-lock adapters, can be provided on distal ends of the extension tubes 48, 50, respectively, opposite to the ends of the extension tubes secured to the hub 42. Each extension tube 48, 50 is in fluid communication with one of the lumens 14, 16 of the tubular body 12 via an associated fluid passage extending through the hub 42.

A tubular, anti-microbial sleeve 60 is disposed on the tubular body 12. The sleeve 60 can be co-extensive with the tubular body 12 of the catheter 10. Preferably, the sleeve 60 is not co-extensive with the tubular body 12, i.e., the sleeve 60 does not extend the entire length of the tubular body 12, but covers only a portion of the tubular body 12. In the catheter 10 shown in FIGS. 1 and 2, the sleeve 60 covers only a portion of the outer surface of the tubular body 12. In the illustrated catheter 10 shown in FIGS. 1 and 2, the sleeve 60 is located between the end 43 of the hub 42 and the end 47 of the cuff 46.

Figure 5:
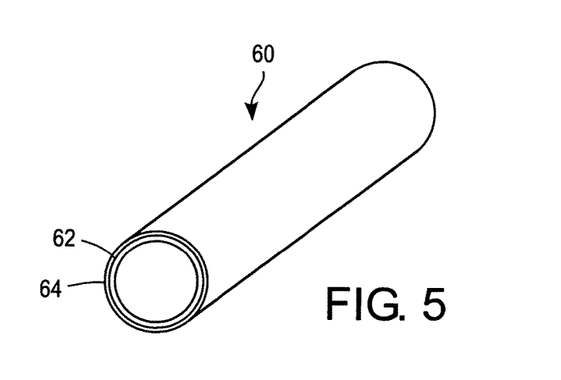
FIG. 5 is a perspective view of an exemplary embodiment of an anti-microbial sleeve.
Figure 6:
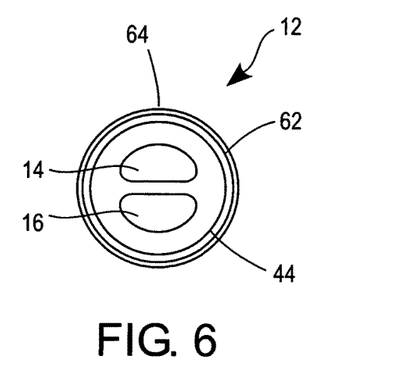
FIG. 6 is a cross-sectional view in the direction of line 6-6 of FIG. 1, showing an exemplary embodiment of an anti-microbial sleeve provided on the tubular body.

As shown in FIGS. 5 and 6, the sleeve 60 has a two-layer construction including an inner layer 62, which is disposed on the outer surface 44 of the tubular body 12, and an outer layer 64 directly overlying the inner layer 42. The sleeve 60 is preferably formed by a co-extrusion process in which the inner layer 62 and outer layer 64 are co-extruded using any suitable extrusion apparatus.

The sleeve 60 contains a water-soluble, anti-microbial agent in the outer layer 64. As used herein, the term "water-soluble, anti-microbial agent" refers to an anti-microbial agent that is substantially completely soluble in aqueous liquid. When the water-soluble, anti-microbial agent contained in the sleeve is exposed to bodily fluids, such as blood or intestinal fluid, and dissolves, a void is formed in the sleeve where the water-soluble, anti-microbial agent previously existed. Because the water-soluble, anti-microbial agent is contained only in the outer layer 64, voids form only in the outer layer 64. By confining voids in only the outer layer 64, swelling of the sleeve 60 due to the anti-microbial agent is minimized. The water-soluble, anti-microbial agent preferably is substantially uniformly distributed throughout the volume of the outer layer 64 so that it is uniformly released when exposed to bodily fluids during use of the catheter 10. Preferably, the water-soluble, anti-microbial agent is not contained in any other portion of the catheter 10 in addition to the outer layer 64 of the sleeve 60.

In an exemplary embodiment, the catheter 10 can also comprise at least one non-water-soluble, anti-microbial agent located, for example, in the tubular body 12. The non-water-soluble, anti-microbial agent can be any suitable antimicrobial agent well known in the art.

The catheter 10 is constructed such that the tubular body 12 is partially implanted in a patient's body (e.g., in the subcutaneous tunnel tract) with a portion of the length of the sleeve 60 implanted, and with the remainder of the sleeve 60 positioned externally of the entry site of the catheter 10. The sleeve 60 is not inserted into a blood vessel. Preferably, the water-soluble, anti-microbial agent contained in the sleeve 60 is effective to reduce the risk of catheter-related, tunnel tract and exit site microbial infections during usage of the catheter 10.

The inner layer 62 and the outer layer 64 of the sleeve 60 can be made of any suitable material (i.e., in addition to the water-soluble, anti-microbial agent contained in the outer layer 64), provided that the material forming the outer layer 64 permits release of the water-soluble, anti-microbial agent. For example, the inner layer 62 and the outer layer 64 of the sleeve 60 can be composed of a hydrophilic material. In one exemplary embodiment of the catheter 10, the inner layer 62 and the outer layer 64 comprise the same hydrophilic material. In another exemplary embodiment of the catheter 10, the inner layer 62 and the outer layer 64 comprise different hydrophilic materials. The hydrophilic material forming the outer layer 64 can have desired hydrophilic characteristics to affect the rate of release of the water-soluble, anti-microbial agent contained in the outer layer 64.

Hydrophilic polyurethanes are an exemplary hydrophilic material that can be used to make the inner layer 62 and outer layer 64 of the sleeve 60. In an exemplary embodiment, the inner layer 62 and optionally the outer layer 64 of the sleeve 60 are made from the same or different aliphatic, polycarbonate-based thermoplastic polyurethanes (TPU). In another embodiment, the outer layer 64 of the sleeve 60 can be made from an aliphatic, polyether-based thermoplastic polyurethane, and the inner layer 62 of the sleeve 60 can be made from a different polyurethane. Exemplary aliphatic, polycarbonate-based thermoplastic polyurethanes that can be used to make the sleeve 60 are formulated to absorb a water content of about 0.3% to about 1% of the weight of the dry resin. Exemplary aliphatic, polyether-based thermoplastic polyurethanes that can be used to make the sleeve 60 are formulated to absorb a water content of about 20% to about 100% or even higher of the weight of the dry resin.

During use of the catheter, the water-soluble, anti-microbial agent contained in the outer layer 64 of the sleeve 60 is exposed to liquids, such as bodily fluids. This exposure to liquids causes the water-soluble, anti-microbial agent to be released from the outer layer 64, resulting in void formation in the outer layer 64. The hydrophilic material of the outer layer 64 of the sleeve 60 absorbs moisture when exposed to the liquids. Preferably, the inner layer 62 of the sleeve 60 has a sufficient thickness (and strength) relative to the thickness of the outer layer 64 to reduce swelling and anchor the outer layer 64 (and therefore reduce an increase in the outer diameter and length of the sleeve 60) when the outer layer 64 absorbs moisture. Preferably, the thickness of the inner layer 62 is greater than the thickness of the outer layer 64. More preferably, the thickness of the inner layer 62 of the sleeve 60 is at least about three times the thickness of the outer layer 64 (e.g., at least about three times, four times, five times, six times, or more) to reduce swelling of the outer layer 64 when exposed to moisture. The relative thickness of the inner layer 62 and outer layer 64 of the sleeve 60 will vary according to catheter size and construction.

The sleeve 60 can have any suitable length in the catheter 10. As described above, the sleeve preferably is not co-extensive with the tubular body 12. For example, the sleeve 60 can have a length of about 50 mm. The sleeve 60 can typically have an outer diameter of about 5 mm.

The sleeve 60 is bonded to the outer surface 44 of the tubular body 12 to fix the sleeve 60 in place on the catheter 10. Any of well-known methods of bonding polymeric materials can be used. In an exemplary embodiment, the sleeve 60 is adhesively bonded to the outer surface 44 of the tubular body 12. Preferably, at least the proximal end 66 and the distal end 68 of the sleeve 60 are adhesively bonded to the outer surface 44 of the tubular body 12. In an exemplary embodiment, substantially an entire inner surface of the inner layer 62 of the sleeve 60 is adhesively bonded to the outer surface 44 of the tubular body 12. Adhesive can be applied to attach the sleeve 60 to the outer surface 44 of the tubular body 12 by any suitable technique. In an exemplary embodiment, the sleeve 60 is adhesively bonded to the outer surface 44 of the tubular body 12 with a liquid-tight seal between at least the proximal end 66 and the distal end 68 of the sleeve 60 and the outer surface 44.

The water-soluble, anti-microbial agent is contained in the outer layer 64 of the sleeve 60 in an amount effective to provide the desired anti-microbial effect. In an exemplary embodiment, the outer layer 64 of the sleeve 60 contains about 5 wt. % to about 20 wt. % of the water-soluble, anti-microbial agent, preferably about 10 wt. % to about 20 wt. %, and more preferably about 15 wt. % to about 20 wt. %, of the water-soluble, anti-microbial agent.

The water-soluble, anti-microbial agent is preferably in particle form. The particles can have any suitable shape, such as polygonal, spherical, irregular, fibrous and like shapes, or combinations of such different particle shapes. The water-soluble, anti-microbial agent in the outer layer 64 of the sleeve 60 can have any suitable particle size. Generally, a smaller particle dissolves faster than a larger particle.

Accordingly, the particle size of the anti-microbial agent can be selected to provide a desired dissolution rate. In an exemplary embodiment, the water-soluble, anti-microbial agent has a particle size of about 0.001 micron to about 100 microns, preferably from about 0.1 micron to about 50 microns, more preferably from about 4 μm to about 30 μm, such as about 10 μm to about 25 μm.

Preferably, the water-soluble, anti-microbial agent comprises an anti-microbial metal. The water-soluble, anti-microbial agent can supply an anti-microbial metal cation. The anti-microbial metal is preferably substantially incorporated by a water-soluble glass. As used herein, the term "water-soluble glass" refers to any water-soluble glass or glass-like material that can be used to incorporate an anti-microbial agent and is substantially completely soluble in an aqueous liquid. Examples of suitable water-soluble glass materials that can be used in embodiments of the catheters are described in U.S. Pat. No. 5,470,585, WO-A-98/54104, WO-A-99/62834 and WO-A-99/62835 (assigned to Giltech Limited), the entire disclosures of which are hereby incorporated by reference.

Phosphorous pentoxide ($P_2O_5$) is a preferred glass-forming material for use in an exemplary water-soluble glass of the anti-microbial agent. The water-soluble glass can also include other constituents, including alkali metal oxides, alkaline earth metal oxides, lanthanide oxides, carbonates, combinations thereof and the like, as a glass modifier. In an exemplary embodiment, the water-soluble glass comprises phosphorus pentoxide as the principal glass-former, and one or more suitable other constituents, such as sodium oxide ($Na_2O$), calcium oxide (CaO), potassium oxide ($K_2O$), magnesium oxide (MgO), zinc oxide (ZnO), combinations thereof, and the like.

In an exemplary embodiment, the water-soluble glass is a phosphate glass, and the water-soluble, anti-microbial agent comprises a source of silver ions. The source of silver ions may advantageously be introduced during manufacture in various forms including, for example, silver orthophosphate ($Ag_3PO_4$).

In exemplary embodiments of the water-soluble, anti-microbial agent that include silver, the silver content based on the total weight of the anti-microbial agent can be between about 0.01 wt. % to about 90 wt. %, such as about 0.05 wt. % to about 80 wt. %, about 0.10 wt. % to about 75 wt. %, about 0.5 wt. % to 65 wt. %, about 1 wt. % to about 50 wt. %, about 2 wt. % to about 40 wt. %, about 2 wt. % to about 30 wt. %, about 2.5 wt. % to about 20 wt. %, or about 3 wt. % to about 9 wt. %.

The formulation for the outer layer 64 of the sleeve 60 can optionally contain one or more coloring pigments to give the outer layer 64 a desired color on the catheter 10. The formulation can typically comprise about 1 wt. % or less of coloring pigments.

The mode of release for the glass is a function of time, rate and concentration. An optimum rate of release of metal ions into an aqueous environment can be tailored based upon the particular application including the specific function of the released metal. In some cases, the required rate of release can be such that all of the metal added to the system is released in a short period of time, e.g., hours or days, while in other applications all of the metal may be released slowly at a substantially uniform rate over a longer period.

In exemplary embodiments, a multi-stage release profile can be achieved by using one or more water-soluble, anti-microbial agents of varying sizes in the outer layer 64 of the sleeve 60. For example, an exemplary embodiment of a sleeve 60 having multi-stage release can comprise water-soluble, anti-microbial agents in the form of particles that have two or more different, pre-determined particle size ranges. Each particle size range provides a different release stage. Particles in the smallest particle size range can provide an initial, more rapid release stage and particles in one or more larger particle size ranges can provide subsequent, more gradual release stages. In such embodiments, the composition, geometry and/or configuration of the water-soluble, anti-microbial agent contained in the sleeve 60 can vary as long as there are different pre-determined size ranges to provide multiple, corresponding release stages.

As shown in FIGS. 1 to 3, the illustrated catheter 10 can comprise an optional coating 70 containing an anti-thrombogenic agent. The coating 70 is formed on the outer surface 44 of the tubular body 12. In an exemplary embodiment, the coating 70 is formed on the outer surface 44 of the tubular body 12 only between end 49 of the cuff 46 and the distal tip 18. The coating 70 is preferably also formed on substantially an entire inner surface of the tubular body 12. In another exemplary embodiment, a coating containing an anti-thrombogenic agent can be formed on substantially the entire outer surface and inner surface of the catheter.

The anti-thrombogenic agent can be any suitable substance that provides the desired anti-thrombogenic function when applied on the outer surface 44 of the tubular body 12. In an exemplary embodiment, the anti-thrombogenic substance is heparin.

In another exemplary embodiment, the anti-thrombogenic agent of the coating 70 is an anti-thrombogenic/non-thrombogenic composition, i.e., the composition has both an anti-thrombogenic function and a non-thrombogenic function and can dissolve existing clots and prevent the formation of new clots. One suitable anti-thrombogenic/non-thrombogenic composition that can be used for the coating 70 is BIBA-HEPCOAT available from BioInteractions, Ltd. Suitable anti-thrombogenic/non-thrombogenic polymers that can be used are described in U.S. Pat. No. 6,096,798, the entire disclosure of which is hereby incorporated by reference.

The coating containing the anti-thrombogenic agent or the anti-thrombogenic/non-thrombogenic composition can be formed on the outer surface 44 and the inner surface of the tubular body 12 (or on substantially the entire outer and inner surface of the catheter) by any suitable coating technique.

EXAMPLES

Example 1: Preparation of Anti-Microbial Sleeve Comprising the Same Hydrophilic Polyurethane in the Inner and Outer Layers A first exemplary embodiment of an anti-microbial sleeve for a catheter is prepared. The sleeve comprises an inner layer made from an aliphatic, polycarbonate-based thermoplastic polyurethane resin (which is described as having a hardness of Shore A 75 to Shore D 72), and an overlying outer layer made from a formulation containing about 81.4 wt. % of the aliphatic, polycarbonate-based thermoplastic polyurethane resin, about 18.5 wt. % of a water-soluble, anti-microbial agent in the form of an anti-microbial powder, and about 1.1 wt. % of coloring additives. The water-soluble, anti-microbial agent is composed of about 20.4 mole % $Na_2O$, about 21.0 mole % MgO, about 9.2 mole % $Ag_2O$ and about 49.4 mole % $P_2O_5$. About 90% of the particles of the water-soluble, anti-microbial agent have a particle size of less than about 25 μm.

The anti-microbial sleeve is manufactured by a co-extrusion process using a main extruder, which forms the inner layer, and a co-extruder, which forms the outer layer of the sleeve. The main extruder and the co-extruder feed extruded material to the same die to produce the two-layer sleeve structure. For the sleeve, the inner layer has an average thickness equal to about three times the average thickness of the outer layer.

Example 2: Preparation of Anti-Microbial Sleeves Comprising Different Hydrophilic Polyurethanes in the Inner and Outer Layers A second exemplary embodiment of an anti-microbial sleeve for a catheter is prepared by a co-extrusion process as described above regarding Example 1. The sleeve includes an inner layer made from an aliphatic, polycarbonate-based thermoplastic polyurethane resin, and an overlying outer layer made from a formulation containing about 85 wt. % of an aliphatic, polyether-based thermoplastic polyurethane resin (which is described as having a hardness of Shore A 90 to Shore D 60) formulated to absorb a water content of about 20% of the weight of the dry resin; and about 15 wt. % of the water-soluble, anti-microbial powder used in Example 1, having an average particle size of about 19 μm. A plurality of sleeves are manufactured by co-extruding the inner layer composition and the outer layer composition to form the two-layer sleeve construction. For the sleeves, the inner layer has a nominal thickness of about 0.38 mm, and the outer layer has a nominal thickness of about 0.13 mm. The sleeves have a length of about 50 mm.

Example 3: Sleeve Silver Release Profiles

Figure 7:
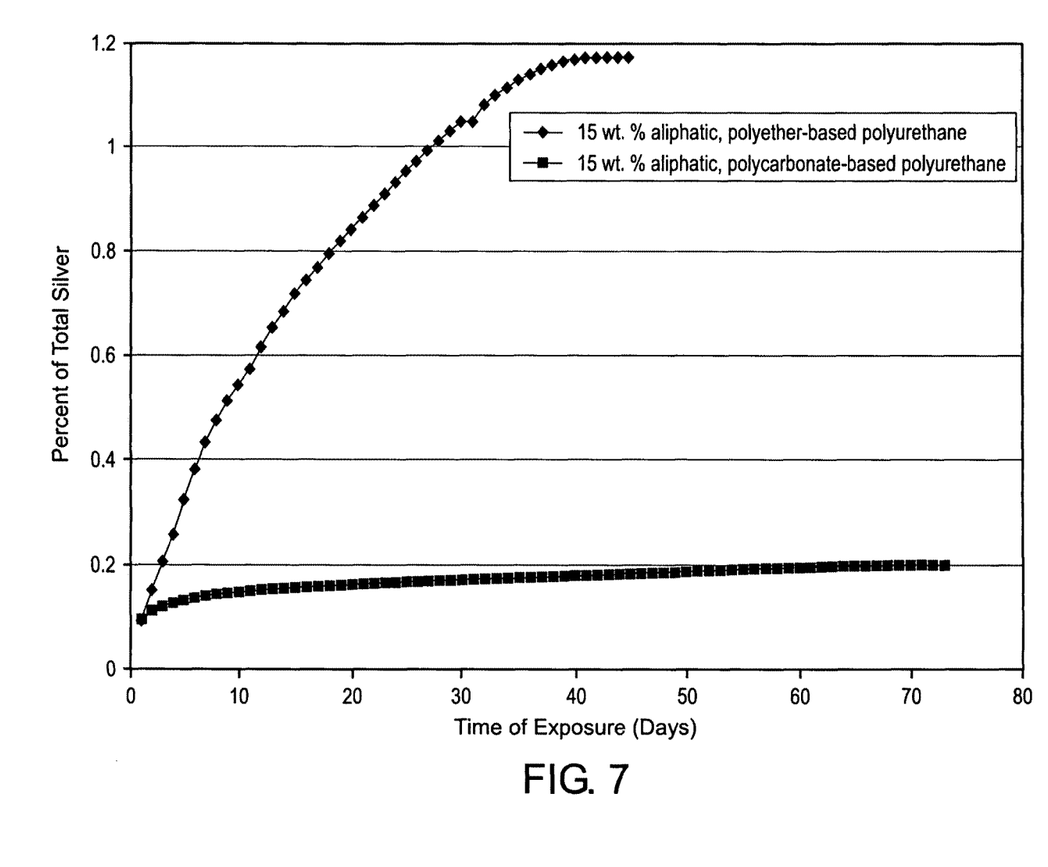
FIG. 7 shows the relationship between % of silver released and time for anti-microbial sleeves comprising aliphatic, polycarbonate-based thermoplastic polyurethane (□) and aliphatic, polyether-based thermoplastic polyurethane (◇) in the sleeve outer layer.

The sleeves of Examples 1 and 2 are subjected to elution testing to evaluate silver release from the outer layer of the sleeves. The sleeves are placed in about 50 mL of de-ionized water at a temperature of about 37° C. FIG. 7 shows the percent of the total silver content of the sleeve that is released as a function of time for the sleeves of Examples 1 and 2. As shown in FIG. 7, the sleeve of Example 2 (made using aliphatic, polyether-based thermoplastic polyurethane for the outer layer) releases a significantly higher percent of the total silver during the test period as compared to the sleeve of Example 1 (made using aliphatic, polycarbonate-based thermoplastic resin for the outer layer) due to the outer layer of the sleeve of Example 2 being more hydrophilic and thus able to absorb more water and accordingly expose the water-soluble, anti-microbial agent to a higher level of water than the polyurethane of the outer layer of the sleeve of Example 1.

Example 4: Sleeve Swelling Behavior

Single-layer and two-layer sleeves are tested to determine the swelling behavior of the sleeves in a liquid (de-ionized water). A plurality of each of three different sleeve constructions are prepared. The first sleeve construction is an extruded, single-layer sleeve made from an aliphatic, polycarbonate-based thermoplastic polyurethane resin without a water-soluble, anti-microbial agent. The first sleeve has a thickness of about 0.25 mm. The second sleeve construction is an extruded, single-layer sleeve made from an aliphatic, polycarbonate-based thermoplastic polyurethane resin with a water-soluble, anti-microbial agent contained in the sleeve. The second sleeve has a thickness of about 0.25 mm. The second sleeve is made from a formulation of about 85 wt. % of the aliphatic, polycarbonate-based thermoplastic polyurethane resin, and about 15 wt. % of the water-soluble, anti-microbial powder composition used in Example 1, having an average particle size of about 19 μm. The third sleeve construction is a co-extruded, two-layer sleeve including an inner layer made from the aliphatic, polycarbonate-based thermoplastic polyurethane resin without a water-soluble, anti-microbial agent, and an outer layer made from a formulation of the same polyurethane resin and a water-soluble, anti-microbial agent. The outer layer formulation of the third sleeve contains about 85 wt. % of the aliphatic, polycarbonate-based thermoplastic polyurethane resin, and about 15 wt. % of the water-soluble, anti-microbial powder composition used in Example 1, having an average particle size of about 19 μm. In the third sleeve, the inner layer has a thickness of about 0.38 mm and the outer layer has a thickness of about 0.13 mm.

Figure 8:
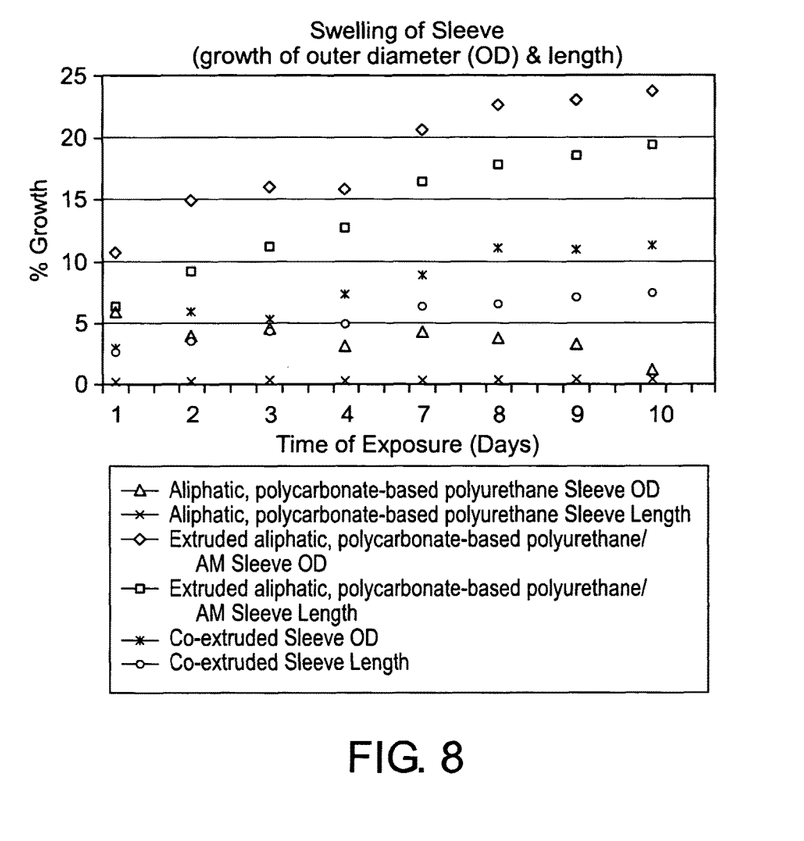
FIG. 8 shows the relationship between % growth versus time of exposure to water for sleeves containing, and sleeves not containing, a water-soluble, anti-microbial agent.

The first, second and third sleeves are placed in de-ionized water, and are analyzed at one-day increments to determine the amount of swelling (growth) of the sleeves due to the exposure to water. The swelling is determined by comparing the original length and outer diameter of each sleeve to the same dimensions after exposure to water. As shown in FIG. 8, the first sleeves having a single-layer construction without a water-soluble, anti-microbial agent exhibited minimal increase in length and a maximum of about 6% increase in outer diameter. The second sleeves having a single-layer construction with a water-soluble, anti-microbial agent exhibited the highest percent increase in length and outer diameter of the sleeves. The results for the second sleeves demonstrate that dissolution of the water-soluble, anti-microbial agent contained in the sleeve leaves voids in the sleeve, which lead to swelling of the sleeve. The third sleeves having a two-layer construction a water-soluble, anti-microbial agent contained in the outer layer exhibited a lower percent increase both in length and outer diameter as compared to the second sleeves, which did not include an inner layer. The results for the third sleeves demonstrate that securing the layer containing the water-soluble, anti-microbial agent to an underlying layer without the water-soluble, anti-microbial agent reduces the degree of swelling of the sleeves.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A catheter, comprising:
    a tubular body having an outer surface;
    a hub disposed on the outer surface of the tubular body;
    a tissue in-growth cuff disposed on the outer surface of the tubular body distal to the hub; and
    a sleeve disposed on only a portion of the outer surface of the tubular body between the hub and the cuff, the sleeve comprising an outer layer co-extruded on an inner layer, the catheter comprising a water-soluble, anti-microbial agent contained only in the outer layer of the sleeve,
    wherein the inner layer has a thickness at least about three times the thickness of the outer layer to reduce swelling of the sleeve and anchor the outer layer.

2. The catheter of claim 1, wherein the outer layer of the sleeve contains about 5 wt. % to about 20 wt. % of the water-soluble, anti-microbial agent.

3. The catheter of claim 2, wherein the outer layer of the sleeve contains about 15 wt. % to about 20 wt. % of the water-soluble, anti-microbial agent.

4. The catheter of claim 1, wherein the water-soluble, anti-microbial agent has a particle size of about 4 µm to about 30 µm.

5. The catheter of claim 4, wherein the water-soluble, anti-microbial agent has a particle size of about 10 µm to about 25 µm.

6. The catheter of claim 1, wherein the inner layer and the outer layer of the sleeve comprise the same hydrophilic polyurethane.

7. The catheter of claim 6, wherein the hydrophilic polyurethane is an aliphatic, polycarbonate-based thermoplastic polyurethane that can absorb a water content of about 0.3% to about 1% of the weight of dry resin.

8. The catheter of claim 1, wherein the inner layer and the outer layer of the sleeve comprise different hydrophilic polyurethanes.

9. The catheter of claim 8, wherein the outer layer of the sleeve comprises an aliphatic, polyether-based thermoplastic polyurethane that can absorb a water content of about 20% to about 100% of the weight of dry resin.

10. The catheter of claim 1, wherein the water-soluble, anti-microbial agent comprises an anti-microbial metal compound.

11. The catheter of claim 10, wherein the water-soluble, anti-microbial agent comprises a water-soluble glass which incorporates the anti-microbial metal compound.

12. The catheter of claim 1, wherein the water-soluble, anti-microbial agent comprises an anti-microbial silver compound in an amount of about 0.1 wt. % to about 90 wt. %, based on the total weight of the water-soluble, anti-microbial agent.

13. The catheter of claim 1, wherein the water-soluble, anti-microbial agent comprises phosphorus pentoxide and silver oxide.

14. The catheter of claim 1, further comprising a non-water-soluble, antimicrobial agent.

15. The catheter of claim 1, further comprising:
a coating containing an anti-thrombogenic agent disposed on the outer surface of the tubular body only between the cuff and a distal tip of the tubular body and disposed on substantially an entire inner surface of the tubular body.

16. The catheter of claim 1, further comprising a coating containing an anti-thrombogenic agent on substantially an entire outer surface and inner surface of the catheter.

17. The catheter of claim 16, wherein the anti-thrombogenic agent is an anti-thrombogenic/non-thrombogenic composition.

18. The catheter of claim 15, wherein the anti-thrombogenic agent is an anti-thrombogenic/non-thrombogenic composition.

19. The catheter of claim 1, wherein the tubular body comprises multiple lumens.

20. The catheter of claim 19, wherein the tubular body comprises two lumens and a distal tip including slots formed in opposite sides of the tubular body, each lumen communicates with a single slot.

21. The catheter of claim 1, which is a hemodialysis catheter.

22. The catheter of claim 1, wherein the sleeve is adhesively bonded to the outer surface of the tubular body.

23. The catheter of claim 22, wherein substantially an entire inner surface of the inner layer of the sleeve is bonded to the outer surface of the tubular body.

24. The catheter of claim 22, wherein the sleeve comprises a proximal end and a distal end, and the sleeve is adhesively bonded to the outer surface of the tubular body with a liquid-tight seal between at least the proximal end and the distal end of the sleeve and the outer surface.

25. The catheter of claim 1, wherein the water-soluble, anti-microbial agent comprises first particles having a first particle size range and second particles having a second particle size range which is larger than the first particle size range, the first particles having a first release rate and the second particles having a second release rate which is less than the first release rate.

26. A method of making a catheter, comprising:
forming a hub on an outer surface of a tubular body;
applying a tissue in-growth cuff on the outer surface of the tubular body distal to the hub; and
applying a sleeve over only a portion of the outer surface of the tubular body between the hub and the tissue in-growth cuff, the sleeve comprising an outer layer co-extruded on an inner layer, the catheter comprising a water-soluble, anti-microbial agent contained only in the outer layer of the sleeve, wherein the inner layer has a thickness at least about three times the thickness of the outer layer to reduce swelling of the sleeve and anchor the outer layer.

27. The method of claim 26, wherein:
the inner layer and the outer layer of the sleeve comprise the same hydrophilic polyurethane; and
the outer layer of the sleeve contains about 5 wt. % to about 20 wt. % of the antimicrobial agent.

28. The method of claim 27, wherein the hydrophilic polyurethane is an aliphatic, polycarbonate-based thermoplastic polyurethane that can absorb a water content of about 0.3% to about 1% of the weight of dry resin.

29. The method of claim 26, wherein:
the inner layer and the outer layer of the sleeve comprise different hydrophilic polyurethanes; and
the outer layer of the sleeve contains about 5 wt. % to about 20 wt. % of the antimicrobial agent.

30. The method of claim 29, wherein the outer layer of the sleeve comprises an aliphatic, polyether-based thermoplastic polyurethane that can absorb a water content of about 20% to about 100% of the weight of dry resin.

31. The method of claim 26, further comprising applying a coating containing an anti-thrombogenic agent on the outer surface of the tubular body only between the cuff and a distal tip and on substantially an entire inner surface of the tubular body.

32. The method of claim 26, further comprising a coating containing an anti-thrombogenic agent, the coating being on substantially an entire outer surface and inner surface of the catheter.

33. The method of claim 32, wherein the anti-thrombogenic agent is an anti-thrombogenic/non-thrombogenic composition.

34. The method of claim 31, wherein the anti-thrombogenic agent is an anti-thrombogenic/non-thrombogenic composition.

35. The method of claim 21, wherein the water-soluble, anti-microbial agent comprises an anti-microbial metal compound.

36. The method of claim 35, wherein the water-soluble, anti-microbial agent comprises a water-soluble glass which incorporates the anti-microbial metal compound.

37. The method of claim 21, wherein the water-soluble, anti-microbial agent comprises an anti-microbial silver compound in an amount of about 0.1 wt. % to about 90 wt. %, based on the total weight of the water-soluble, anti-microbial agent.

38. The method of claim 21, wherein the water-soluble, anti-microbial agent comprises phosphorus pentoxide and silver oxide.

39. The method of claim 21, wherein the catheter further comprises a non-water-soluble, anti-microbial agent.

40. The method of claim 21, wherein the water-soluble, anti-microbial agent comprises first particles having a first particle size range and second particles having a second particle size range which is larger than the first particle size range, the first particles having a first release rate and the second particles having a second release rate which is less than the first release rate.

41. The method of claim 21, wherein the tubular body comprises multiple lumens.

42. The catheter of claim 1, wherein the tubular body comprises a distal tip and the cuff comprises a second end, the catheter further comprising a coating on the outer surface of the tubular body between the second end of the cuff and the distal tip.

43. The catheter of claim 1, wherein the catheter is constructed such that when the catheter is implanted in a patient's body, a portion of the length of the sleeve is implanted in the patient's body and the remainder of the length of the sleeve remains outside of the patient's body.

44. A catheter comprising:
a tubular body having an outer surface;
a hub disposed on the outer surface of the tubular body;
a tissue in-growth cuff disposed on the outer surface of the tubular body distal to the hub; and
a sleeve disposed on only a portion of the outer surface of the tubular body between the hub and the cuff, the sleeve comprising an outer layer co-extruded on an inner layer, the sleeve comprising a water soluble, anti-microbial agent contained only in the outer layer of the sleeve, thereby reducing swelling of the sleeve.

45. The catheter of claim 44, wherein dissolution of the antimicrobial agent in the outer layer substantially limits voids formed in the sleeve by dissolution of the anti-microbial agent to the outer layer, thereby minimizing swelling of the sleeve.

46. The catheter of claim 1, wherein the outer layer constitutes the outermost layer of the sleeve.

47. The catheter of claim 44, wherein the outer layer constitutes the outermost layer of the sleeve.

48. The catheter of claim 44, wherein the inner layer has a sufficient thickness and strength relative to the thickness of the outer layer to reduce swelling of and anchor the outer layer.

\* \* \* \* \*